US00PP36776P3

(12) United States Plant Patent
Olesen

(10) Patent No.: US PP36,776 P3
(45) Date of Patent: Jul. 1, 2025

(54) ROSE PLANT NAMED 'Poulvic011'

(50) Latin Name: *Rosa hybrida*
Varietal Denomination: Poulvic011

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 73 days.

(21) Appl. No.: 18/831,190

(22) Filed: Sep. 5, 2024

(65) Prior Publication Data

US 2025/0107468 P1 Mar. 27, 2025

(30) Foreign Application Priority Data

Sep. 22, 2023 (QZ) ..... PBR 20231984

(51) Int. Cl.
*A01H 5/02* (2018.01)
*A01H 6/74* (2018.01)

(52) U.S. Cl.
USPC ..... Plt./122

(58) Field of Classification Search
USPC ..... Plt./122, 129, 108
CPC . A01H 5/02; A01H 5/00; A01H 6/749; A01H 6/74
See application file for complete search history.

(56) References Cited

U.S. PATENT DOCUMENTS

PP32,297 P2 * 10/2020 Olesen ..... A01H 6/749 Plt./122

OTHER PUBLICATIONS

CPVO Application Consultation Version 4.21.4 retrieved on Dec. 3, 2024 at https://online.plantvarieties.eu/publicConsultationDetails?registerId=20231984&denomination=poulvic011, 2 pp. (Year: 2024).*

* cited by examiner

*Primary Examiner* — June Hwu

(57) ABSTRACT

A new garden rose plant of the miniature class which has abundant, red flowers and attractive foliage. This new and distinct variety has shown to be uniform and stable in the resulting generations from asexual propagation.

2 Drawing Sheets

Botanical designation: *Rosa hybrida.*

Variety denomination: 'Poulvic011'.

This application claims priority to Plant Breeder's Rights Application Number 2023/1984, which was filed at the Community Plant Variety Rights Office in the European Union on Sep. 22, 2023, the contents of which are hereby incorporated by reference for all purposes.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2018 and the resulting seeds were planted in a controlled environment in Fredensborg, Denmark. The new variety, named 'Poulvic011', originated as a single seedling from the stated cross.

The new variety may be distinguished from its male pollen parent and female seed parent primarily by the following characteristics. The male pollen parent plant has red flowers with over 50 petals while the new variety has red flowers with about 38 petals. The female seed parent plant has red flowers 60 mm in diameter while the new variety has red flowers 100 mm in diameter.

The objective of the hybridization of this rose variety was to create a new and distinct variety with unique qualities, such as:

1. Uniform and abundant red flowers;
2. Vigorous, but compact growth when propagated on its own roots;
3. Exceptional disease resistance.

This combination of qualities is not present in previously available commercial cultivars of this type, known to the inventor, and distinguish 'Poulvic011' from all other varieties of which we are aware.

As part of the rose development program, Mogens N. Olesen germinated the seeds from the aforementioned hybridization during winter of 2018 and conducted evaluations on the resulting seedlings in a controlled environment in Fredensborg, Denmark. 'Poulvic011' was selected in the spring of 2019 by the inventor as a single plant from the progeny of the aforementioned hybridization.

Asexual reproduction of 'Poulvic011' by rooted cuttings was first done by Mogens N. Olesen in the nursery in Fredensborg, Denmark in July 2019. This initial and other subsequent asexual propagations conducted in controlled environments have demonstrated that the characteristics of 'Poulvic011' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulvic011'.

Specifically illustrated in FIG. 1 of the drawings are two open flowers of different stages viewed from above, flower buds at various stages of opening, flower petals detached revealing reproductive flower parts, and sepals detached showing receptacle.

Figure 1:
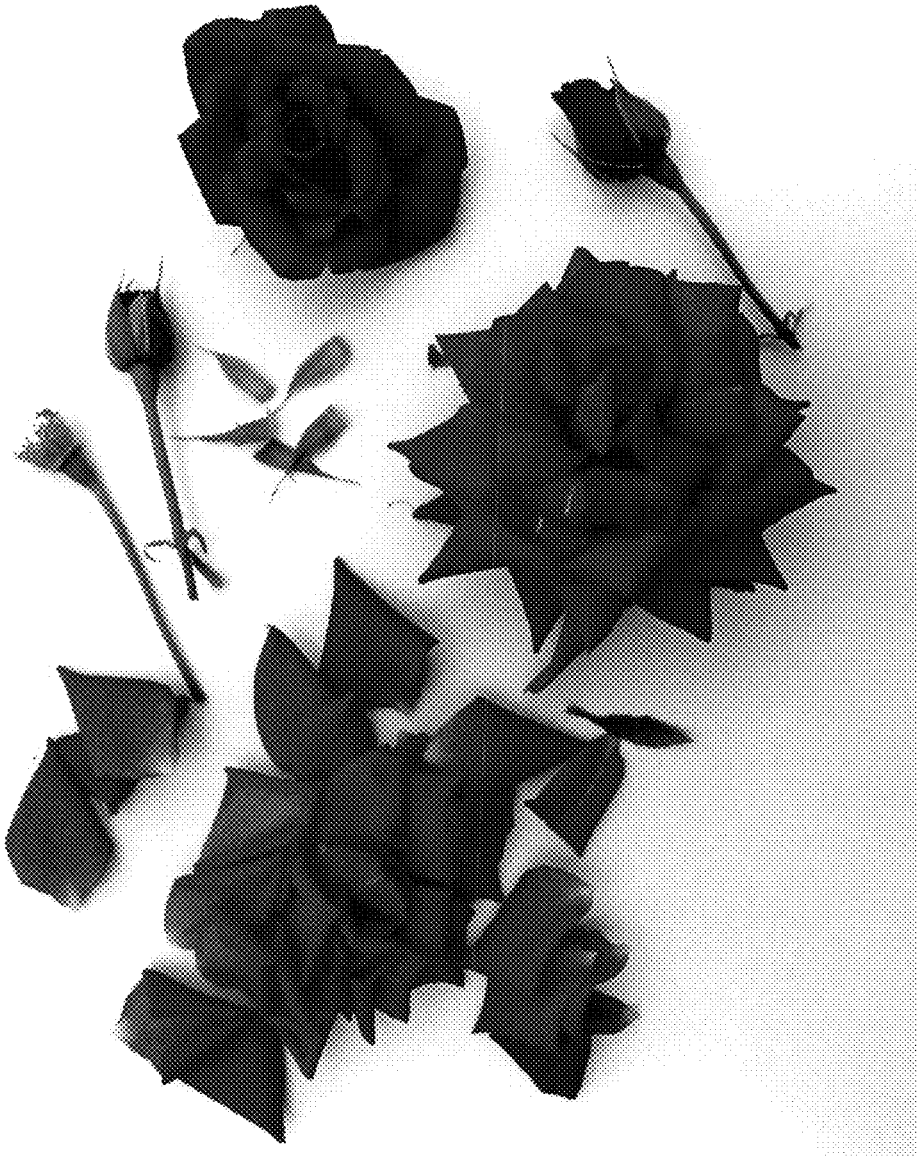
Figure 2:
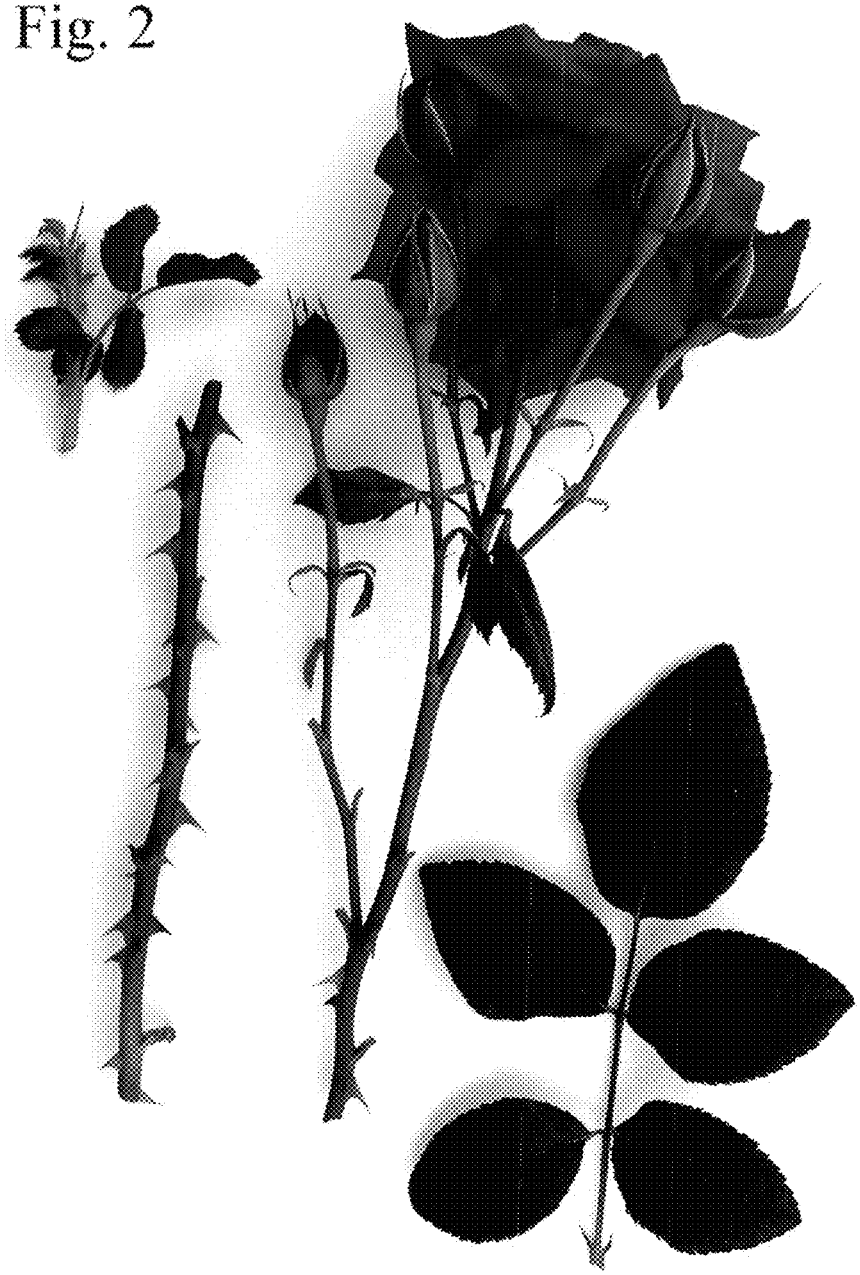

Specifically illustrated in FIG. 2 of the drawings are a cluster of flowers and flower buds on a branch, bare stem showing prickles, mature leaf, and juvenile growth exhibiting anthocyanin. Plants shown are 5 months old.

DETAILED DESCRIPTION OF THE VARIETY

The following is a description of 'Poulvic011', as observed in its growth in an indoor glasshouse nursery in Odense Denmark. Observed plants are 5 months of age, and were grown on their own roots in 19 cm pots. Color references are made using The Royal Horticultural Society (London, England) Colour Chart, 2001, except where common terms of color are used.

For a comparison, several physical characteristics of the rose variety 'Poulpar114', U.S. Plant Pat. No. 32,297 are compared to the claimed plant. While 'Poulvic011' has a moderate floral scent 'Poulpar114' has a light floral scent. The claimed plant has a flower diameter of 100 mm while 'Poulpar114' has a flower diameter of 65 mm. Open flowers of 'Poulvic011' are generally Red Group 53B in color while 'Poulpar114' has a general tonality of Red Group 46B.

FLOWER AND FLOWER BUD

Blooming habit: Continuous.

Flower bud:

- *Size*.—Upon opening, 33 mm in length from base of receptacle to end of bud. Bud diameter is 18 mm.
- *Bud form*.—Ovoid.
- *Bud color*.—As sepals divide petals are Red-Purple Group 59B.
- *Sepal inner surface*.—Color: Yellow-Green Group 144B. Surface: Moderately pubescent.
- *Sepal outer surface*.—Color: Yellow-Green Group 144A. Texture: Smooth.
- *Sepal shape*.—Apex: Cirrhose. Base: Flat at union with receptacle.
- *Sepal margin*.—Margins have weak foliaceous appendages on three of the five sepals.
- *Sepal size*.—About 28 mm long, 7 mm wide.
- *Receptacle*.—Texture: Smooth. Size: 8 mm in height, 6 mm wide. Color: Yellow-Green Group 144A. Shape: Long funnel.
- *Pedicel*.—Surface: Rough with stipitate glands. Length: About 42 mm. Diameter: 2 mm on average. Color: Yellow-Green Group 144A. Strength: Strong.
- *Peduncle*.—Length: 25 to 30 mm. Diameter: About 3 mm. Color: Yellow-Green Group 145A. Texture: Smooth.

Flower bud development: Flower buds are borne both single and in clusters of about 5 flower buds per stem.

Flower bloom:

- *Fragrance*.—Moderate rose scent.
- *Duration*.—The blooms have a duration on the plant of approximately 20 days. Petals fall cleanly away from plant after flowers have fully matured.
- *Size*.—Flower diameter is about 100 mm when open. Flower depth is 50 mm.
- *Flower shape*.—High centered hybrid tea shape with a tightly closed center, opening fully to star shape.
- *Shape of flower, side view*.—The upper portion is convex. The lower portion is flat concave.

Petalage: Under normal conditions, flowers have about 38 petals.

General tonality of flower: Open flowers are Red Group 53B. After flowers have been open for 10 days, the general tonality changes to Red-Purple Group N57A with intonations of Red Group 53B.

Petal color:

- *Upon opening, outer and inner petals*.—Upper surface: Red Group 46B. Yellow Group 9A at base of the petal. Lower surface: Middle and marginal zone are Red Group 53C. Basal zone Yellow Group 4A.
- *After opening, outer and inner petals*.—Upper surface: Red-Purple Group N57A. Basal zone point of attachment Yellow Group 4D. Lower surface: Red-Purple Group 58C with streaks of Red-Purple Group 62D. Basal zone point of attachment Yellow Group 4D.

Petals:

- *Petal reflex*.—Strong, bilateral.
- *Margin*.—Several clefts in the margin. Moderate undulations.
- *Shape*.—Broad and elliptic. Apex shape: Rounded. Base shape: Rounded or acute.
- *Size*.—About 50 mm (l)×42 mm (w).
- *Texture*.—Smooth.
- *Thickness*.—Average.

Petaloids:

- *Size*.—30 mm (l) by 22 mm (w).
- *Quantity*.—4 to 6.
- *Shape*.—Elliptical with an acute base and rounded apices.
- *Color*.—Upper surface Red Group 53B. Lower surface Red Group 53C.

Reproductive flower parts:

- *Pollen*.—None observed.
- *Anthers*.—Size: 2 mm in length. Color: Yellow Group 13C. Quantity: 35 on average.
- *Filaments*.—Color: Yellow-Orange Group 22A. Length: 8 mm.
- *Pistils*.—Length: 5 mm. Quantity: 26 on average.
- *Stigmas*.—Color: Yellow-White Group 158A
- *Styles*.—Color: Green-White Group 157A with intonations of Red-Purple Group 63B.
- *Location of stigmas*.—Inferior in location relative to the length of the filaments and the height of the anthers.
- *Hips*.—None Observed.

PLANT

Plant growth: Upright and compact. Plants are about 27 cm in height, and 25 cm wide.

Stems:

- *Color of juvenile growth*.—Yellow-Green Group 144B.
- *Color of mature growth*.—Yellow-Green Group 144A.
- *Length*.—Canes are about 22 cm from the base of the plant to the flowering portion.

*Diameter*.—About 6 mm.

*Internodes*.—On mature canes about 26 mm between nodes.

*Surface texture*.—Young wood: Smooth. Older wood: Smooth.

Long prickles:

*Incidence*.—About 12 prickles per 10 cm of stem.

*Size*.—Average length of prickles on mature stems is 9 mm.

*Shape*.—Upper portion is linear. Lower portion is deep concave.

*Color*.—Juvenile prickles: Yellow-Green Group 144A. Mature prickles: Greyed-Orange Group 166C with intonations of Yellow-Green Group 144A.

Plant foliage:

*Compound leaf*.—180 mm (l)×120 (w).

*Quantity*.—3 leaves per 10 cm of stem on average.

*Leaf bearing angle to the stem*.—45 degrees.

*Color of juvenile foliage*.—Upper side: Yellow-Green Group 144A. Lower side: Yellow-Green Group 144B.

*Color of mature foliage*.—Upper side: Yellow-Green Group 147A. Lower side: Yellow-Green Group 146B.

Plant leaves and leaflets:

*Stipules*.—Size: 11 mm long, 4 mm wide. Quantity: 2 per compound leaf. Shape: Linear, slightly broad based with outward extending apices. Margins: Finely serrated. Color: Yellow-Green Group 144A.

*Petiole*.—Length: 40 mm. Diameter: 1.5 mm. Upper surface color: Yellow-Green Group 144A. Lower surface color: Yellow-Green Group 144A.

*Rachis*.—Length: About 60 mm. Upper surface color: Yellow-Green Group 144A. Lower surface color: Yellow-Green Group 144A.

*Leaflet*.—Quantity: Normally 5 leaflets. Margins: Serrated. Size: Terminal leaflets are about 81 mm long, 50 mm wide. Shape: Generally elliptical. Base: Rounded. Apex: Acute. Texture: Smooth. Thickness: Average. Arrangement: Odd pinnate. Venation: Reticulate. Glossiness: Moderately glossy.

Disease resistance: Above average resistance to powdery mildew *Sphaerotheca pannosa* var. *rosae*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant named 'Poulvic011' substantially as described and illustrated herein.

* * * * *